(12) United States Patent
Pfrengle et al.

(10) Patent No.: US 8,853,225 B2
(45) Date of Patent: Oct. 7, 2014

(54) 9-[4-(3-CHLORO-2-FLUORO-PHENYLAMINO)-7-METHOXY-QUINAZOLINE-6-YLOXY]-1,4-DIAZA-SPIRO[5.5] UNDECANE-5-ONE DIMALEATE, USE THEREOF AS A MEDICAMENT AND METHOD FOR THE PRODUCTION THEREOF

(75) Inventors: Waldermar Pfrengle, Biberach an der Riss (DE); Guenther Huchler, Hochdorf (DE); Markus Ostermeier, Biberach an der Riss (DE); Peter Sieger, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 142 days.

(21) Appl. No.: 13/359,807

(22) Filed: Jan. 27, 2012

(65) Prior Publication Data
US 2013/0030003 A1     Jan. 31, 2013

(30) Foreign Application Priority Data
Feb. 1, 2011    (EP) .................................. 11152895

(51) Int. Cl.
*A01N 43/54*    (2006.01)
*A61K 31/517*   (2006.01)
*C07D 239/72*   (2006.01)
*C07D 401/00*   (2006.01)

(52) U.S. Cl.
USPC ................. 514/266.2; 544/283; 544/284

(58) Field of Classification Search
USPC ............. 544/283, 284; 514/266.1, 266.2
See application file for complete search history.

(56) References Cited

U.S. PATENT DOCUMENTS

| | | | |
|---|---|---|---|
| 8,497,369 B2 * | 7/2013 | Himmelsbach et al. | ...... 544/253 |
| 2009/0170908 A1 | 7/2009 | Shimada et al. | |
| 2011/0046148 A1 | 2/2011 | Himmelsbach et al. | |
| 2011/0183987 A1 | 7/2011 | Ostermeier et al. | |
| 2011/0281860 A1 * | 11/2011 | Jung | ........................... 514/230.8 |
| 2013/0030003 A1 | 1/2013 | Pfrengle et al. | |

FOREIGN PATENT DOCUMENTS

| | | |
|---|---|---|
| EP | 2289881 A1 | 3/2011 |
| WO | 03082290 A1 | 10/2003 |
| WO | 03082831 A1 | 10/2003 |
| WO | 2006034015 A1 | 3/2006 |
| WO | 2009098061 A1 | 8/2009 |
| WO | 2010026029 A1 | 3/2010 |
| WO | 2011015526 A1 | 2/2011 |
| WO | 2012104206 A1 | 8/2012 |

OTHER PUBLICATIONS

European Search Report for EP 11 15 2895 completed May 4, 2011.
International Search Report for PCT/EP2009/000805 mailed May 8, 2009.
International Search Report for PCT/EP2010/061096 mailed Nov. 16, 2010.
International Search Report for PCT/EP2012/051298 mailed Mar. 8, 2012.
Kumar, Lokesh, et al., "Salt Selection in Drug Development" Pharmaceutical Technology, Advanstar Communications, Inc. (2008) vol. 32, No. 3 pp. 128-146.

* cited by examiner

*Primary Examiner* — Paul V. Ward
(74) *Attorney, Agent, or Firm* — Michael P. Morris; Edward S. Lazer

(57) ABSTRACT

The present invention relates to a compound of formula (I),

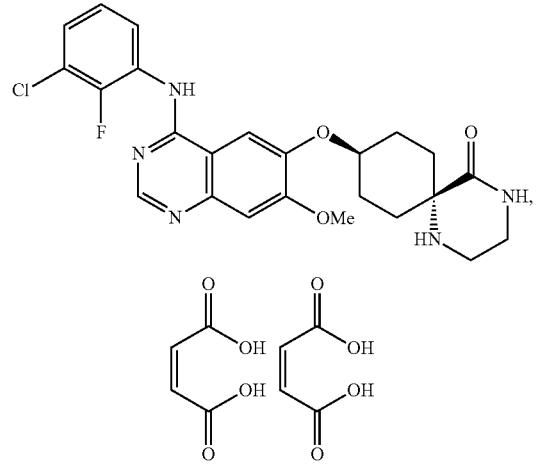

(I)

which has valuable pharmacological properties, particularly an inhibiting effect on signal transduction mediated by tyrosine kinases, processes for stereoselectively preparing these compounds, particularly pharmaceutical formulations suitable for inhalation and their use for the treatment of diseases, particularly tumoral diseases, benign prostatic hyperplasia and diseases of the lungs and airways.

4 Claims, 3 Drawing Sheets

Figure 1: X-ray powder diagram of compound (I)
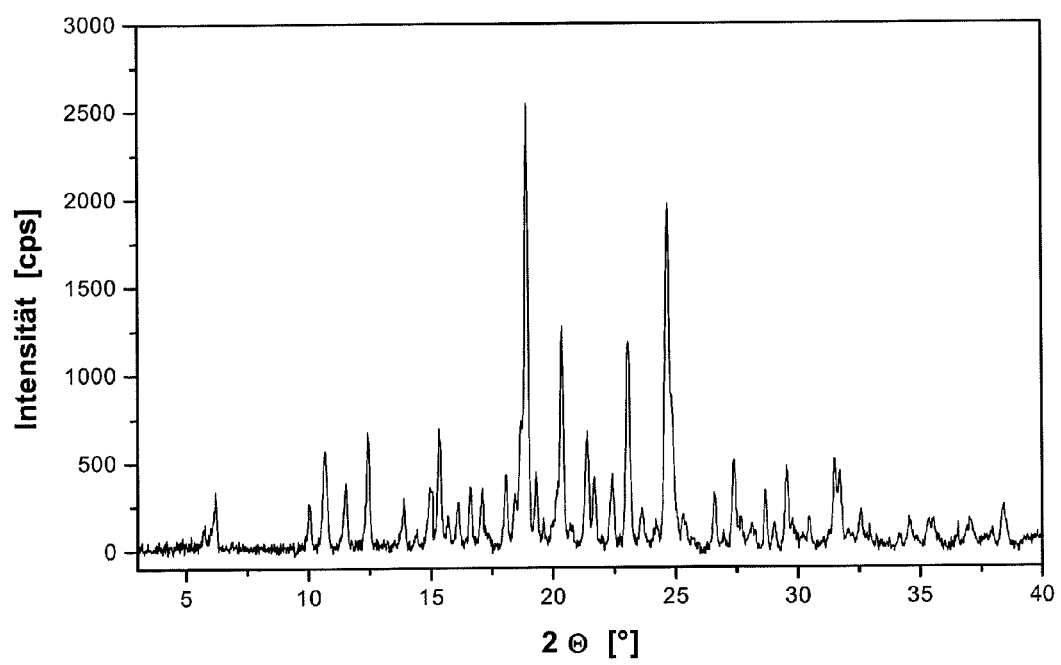

Figure 2: DSC/TG schemes of compound (I)
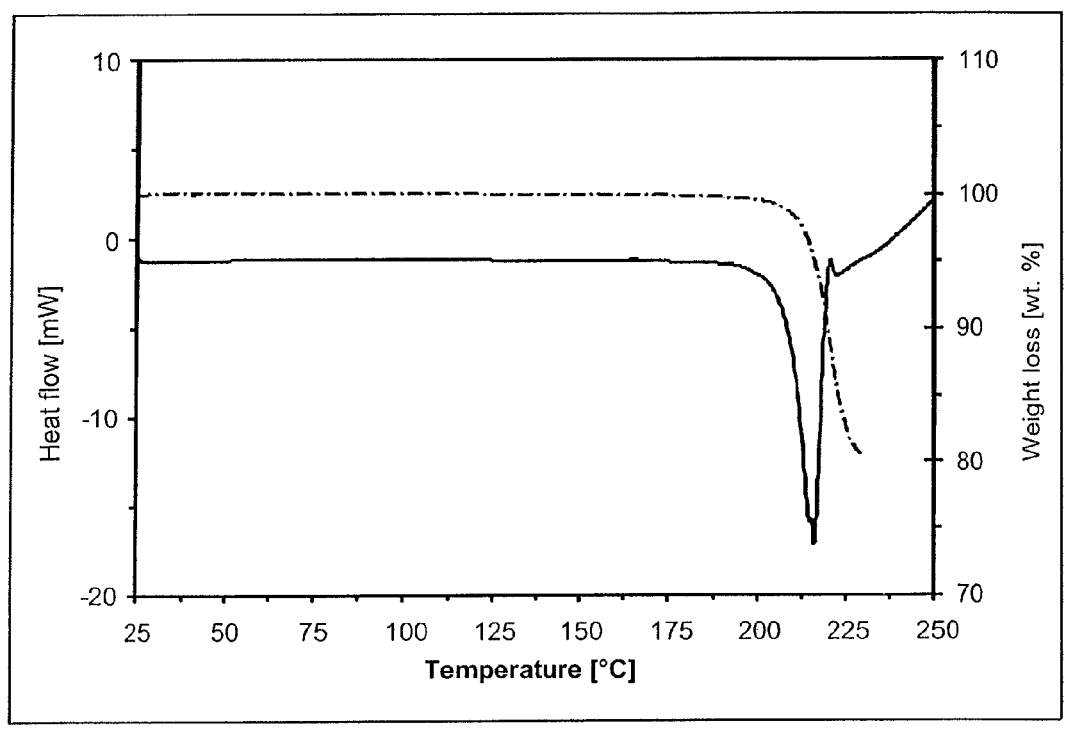

Figure 3: Sorption isotherms of compound (I)
a) Kinetic plot
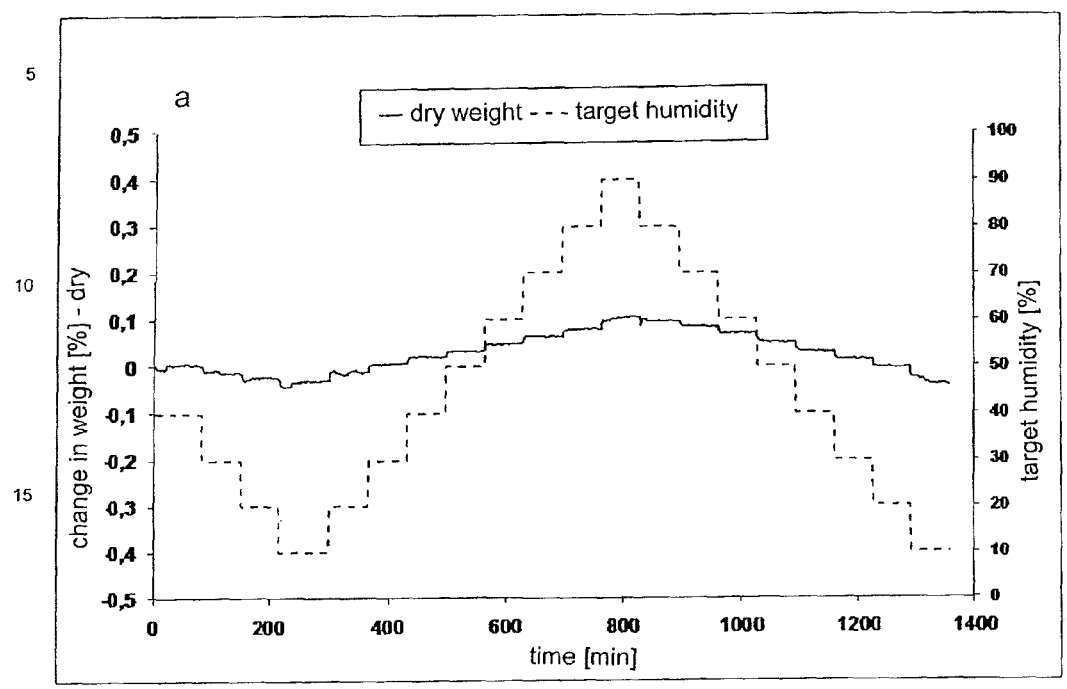

9-[4-(3-CHLORO-2-FLUORO-PHENYLAMINO)-7-METHOXY-QUINAZOLINE-6-YLOXY]-1,4-DIAZA-SPIRO[5.5] UNDECANE-5-ONE DIMALEATE, USE THEREOF AS A MEDICAMENT AND METHOD FOR THE PRODUCTION THEREOF

The present invention relates to the compound of formula (I),

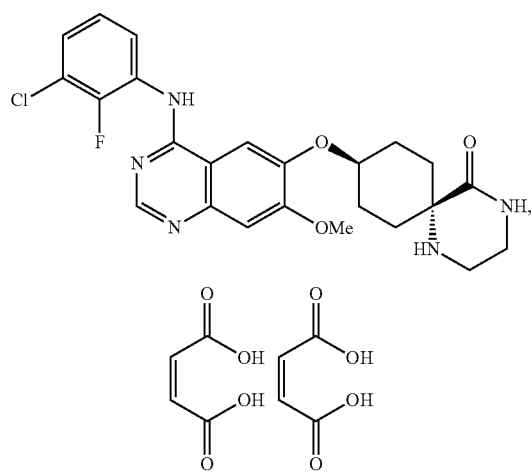

which has valuable pharmacological properties, particularly an inhibiting effect on signal transduction mediated by tyrosine kinases, processes for stereoselectively preparing this compound, particularly pharmaceutical formulations suitable for inhalation and their use for the treatment of diseases, particularly tumoral diseases, benign prostatic hyperplasia and diseases of the lungs and airways.

BACKGROUND TO THE INVENTION

Quinazoline derivatives are known from the prior art as active substances for example for the treatment of tumoral diseases and also diseases of the lungs and airways. Processes for preparing quinazoline derivatives are described in WO03082290 and WO07068552. WO2009098061 discloses the base (compound (II)) of the dimaleate salt according to the invention (compound (I)).

The aim of the present invention is to provide a salt of 9-[4-(3-chloro-2-fluorophenylamino)-7-methoxy-quinazolin-6-yloxy]-1,4-diaza-spiro[5.5]undecan-5-one which by virtue of its pharmaceutical efficacy as a tyrosine-kinase inhibitor is suitable for use in the therapeutic field, i.e. for the treatment of pathophysiological processes that are caused by the hyperfunction of tyrosine-kinases.

A further aim is to provide a compound that meets the requirements for physical and chemical stability and other properties, such as for example crystalline stability, the absence of polymorphism and low hygroscopicity, particularly with regard to the absence of polymorphism, that are imposed on an active substance of a medicament. Another aim of the present invention is to provide a stereoselective process for preparing the compound according to the invention.

DESCRIPTION OF THE DRAWINGS

FIG. 1: X-ray powder diagram of compound (I)
FIG. 2: DSC/TG schemes of compound (I)
FIG. 3: Sorption isotherms of compound (I): a.) kinetic plot, b.) isothermic plot

DETAILED DESCRIPTION OF THE INVENTION

The present invention solves the above-mentioned problems by providing the compound of formula (I) that is suitable in particular for oral administration, which is highly crystalline, has low hygroscopicity and low polymorphism, the pharmaceutical formulation thereof and the method of synthesis described hereinafter. By crystalline stability is meant, within the scope of the present invention, that X-ray powder diagrams of the compound of formula (I) have sharp reflections with high intensity up to the upper 2θ range, preferably up to 20-40° 2θ.

By low hygroscopicity is meant, within the scope of the present invention, that in sorption experiments on the compound of formula (I) a water uptake of less than 1% is observed in the humidity range of 10-90% investigated.

By low polymorphism is meant, within the scope of the present invention, that after recrystallization from different solvents of the compound of formula (I) a maximum of 5 other crystal modifications, preferably a maximum of 3 other crystal modifications, particularly preferably no other crystal modifications are obtained.

The invention relates to a compound of formula (I)

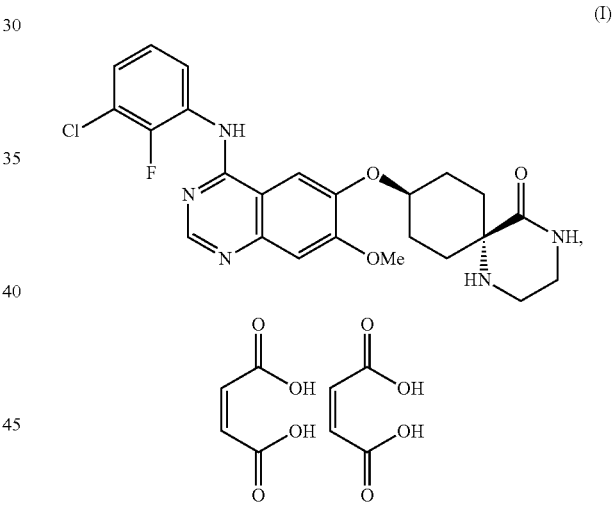

optionally in the form of the tautomers, solvates or hydrates thereof.

A crystalline compound of formula (I) is preferred wherein reflections occur in the X-ray powder diagram with $d_{hkl}$ values of 7.11, 5.77, 4.69, 4.36, 4.15, 3.85 and 3.61 Å.

The invention further relates to the above-mentioned compound for use as a medicament, preferably for the treatment of inflammatory or allergic diseases of the airways, particularly preferably for the treatment of chronic obstructive bronchitis (COPD) and/or chronic bronchitis.

The compound of formula (I) is useful for treating diseases, preferably selected from among acute bronchitis, bronchitis caused by bacterial or viral infection or fungi or helminths, allergic bronchitis, toxic bronchitis, asthma (intrinsic or allergic), paediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, e.g. radiation-induced or caused by aspiration or infectious pneumonitis, collagenoses such as lupus erythematodes, systemic scleroderma, sarcoidosis and Boeck's disease, and for treating complications in asthma and COPD triggered by viral, bacterial or other causes, for treating viral or bacterial infections of the airways or lungs.

It is also preferred to use the compound of formula (I) in cases of inflammatory or allergic complaints in which autoimmune reactions are involved.

It is also preferred to use the compounds of formula (I) in cases of a disease in the form of benign or malignant tumours.

The invention further relates to a process for the stereoselective preparation of the compound of formula (I), optionally in the form of the tautomers, solvates or hydrates thereof:

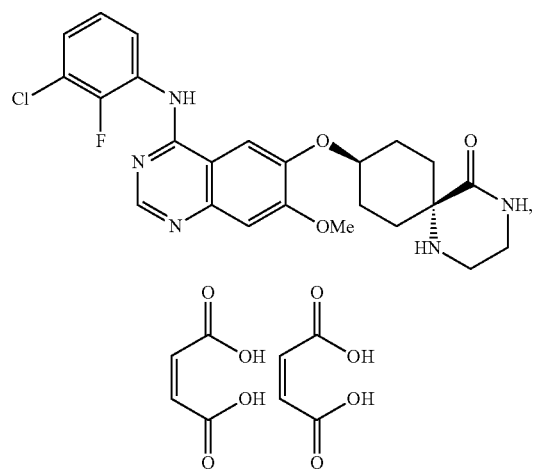
(I)

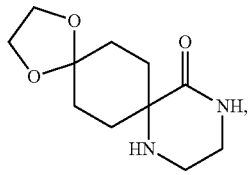

the process comprising reaction steps (A) to (M), wherein (A) denotes the reaction of 1,4-cyclohexanedione-monoethyleneketal to form a compound of formula (1)

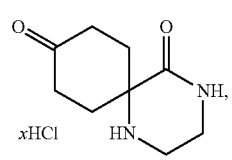
(1)

(B) is the reaction of a compound of formula (1) to form the compound of formula (2)

(2)

xHCl (C) is the reaction of a compound of formula (2) to form the compound of formula (3)

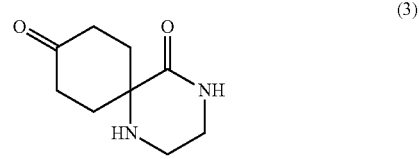 [SMILES: O=C1CCC2(CC1)NCCNC2=O]
(3)

(D) is the reaction of a compound of formula (3) with a protective group reagent to form the compound of formula (4)

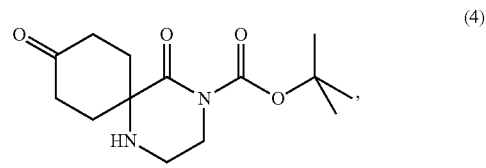 [SMILES: CC(C)(C)OC(=O)N1CCNC2(CCC(=O)CC2)C1=O]
(4)

(E) is the reduction of a compound of formula (4) to form the compound of formula (5)

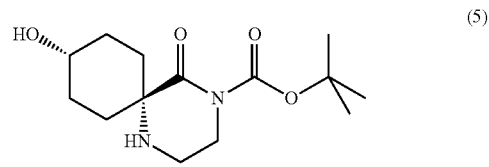 [SMILES: CC(C)(C)OC(=O)N1CCN[C@]2(CC[C@@H](O)CC2)C1=O]
(5)

(F) is the reaction of a compound of formula (5) to form a compound of formula (6)

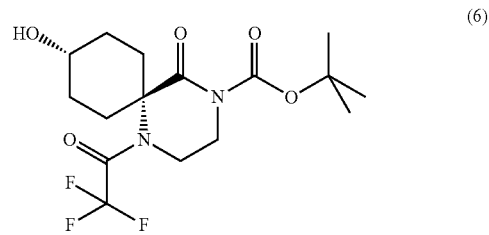 [SMILES: CC(C)(C)OC(=O)N1CCN(C(=O)C(F)(F)F)[C@]2(CC[C@@H](O)CC2)C1=O]
(6)

(G) is the reaction of a compound of formula (6) with a compound of formula (13) to form a compound of formula (7)

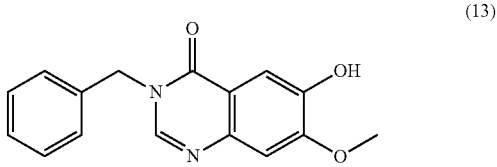
(13)

-continued (7)

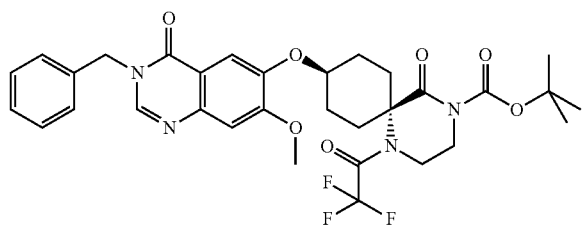

(H) is the reaction of a compound of formula (7) to form a compound of formula (8a) or its tautomeric form (8b), (8a)

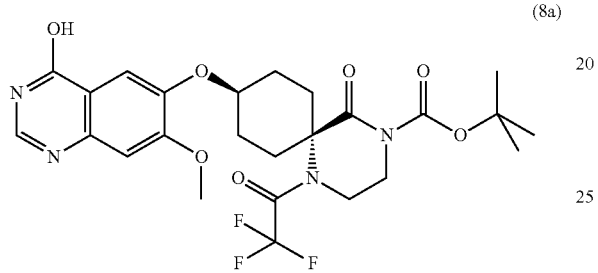

(8b)

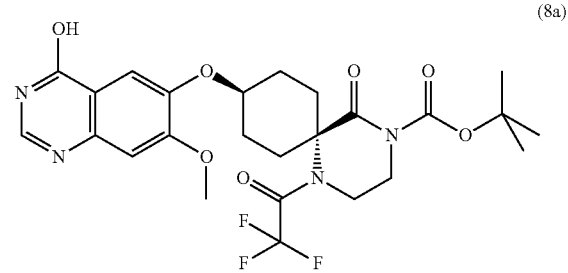 [SMILES: COc1cc2ncnc(Cl)c2cc1O[C@H]1CC[C@]2(CC1)C(=O)N(C(=O)OC(C)(C)C)CCN2C(=O)C(F)(F)F]

(I) is the chlorination of the compound of formula (8a) or (8b) to form a compound of formula (9)

(9)

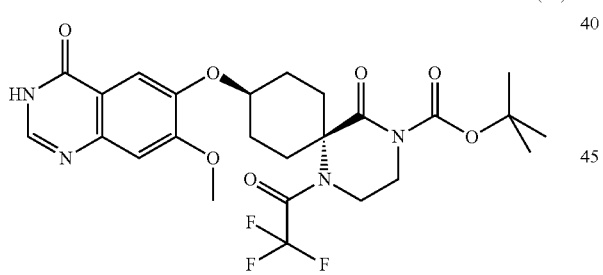

(J)+(K) are the reaction of the compound of formula (9) with 3-chloro-2-fluoraniline and the cleaving of a protective group to form a compound of formula (11) or (11A)

(11)

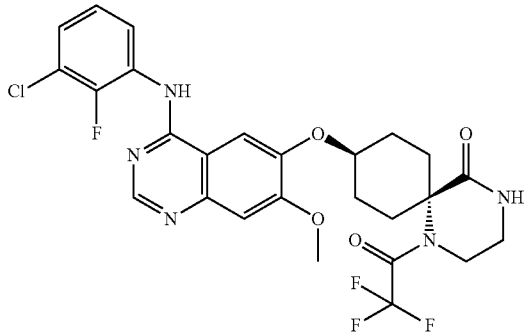

(11A)

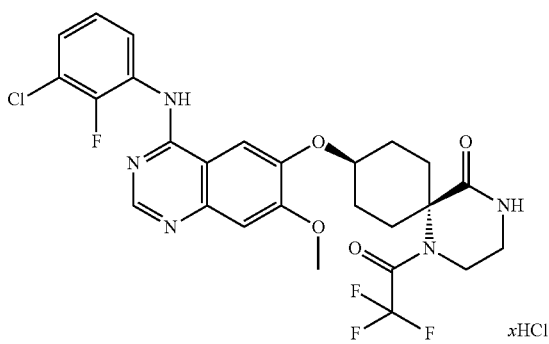

·xHCl (L) is the cleaving of another protective group to form the compound of formula (II)

(II)

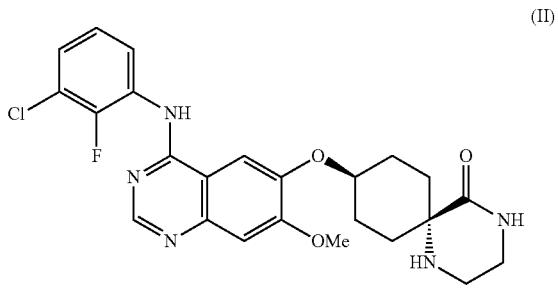 [SMILES: COc1cc2ncnc(Nc3cccc(Cl)c3F)c2cc1O[C@H]1CC[C@@]2(CC1)NCCNC2=O]

(M) is the reaction of the compound of formula (II) with maleic acid to form a compound of formula (I), optionally in the form of the tautomers, solvates or hydrates thereof,

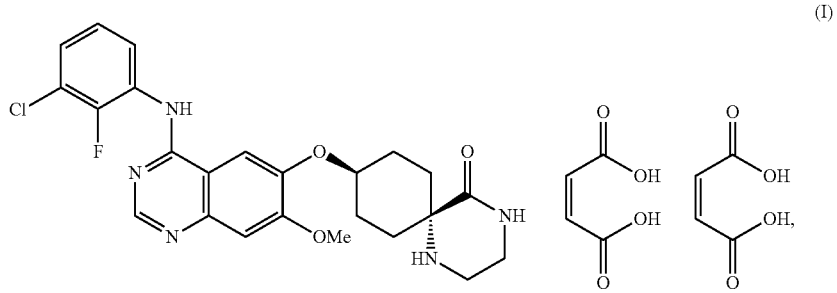

(I)

while process steps (A) to (M) take place successively in the sequence indicated.

The invention further relates to a process for the stereoselective preparation of the compound of formula (I), optionally in the form of the tautomers, solvates or hydrates thereof, comprising process steps (A) to (M), wherein process steps (J+K) are replaced by steps (N+O), where (N+O) is the cleaving of a protective group of the compound of formula (9) to form the compound of formula (12) and subsequent reaction with 3-chloro-2-fluoraniline to form the compound of formula (11) or (11A)

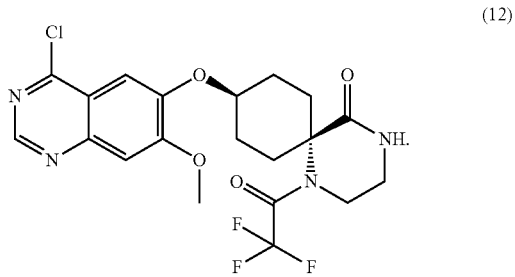 [SMILES: COc1cc2ncnc(Cl)c2cc1O[C@H]1CC[C@]2(CC1)C(=O)NCCN2C(=O)C(F)(F)F]

(12)

In a preferred process for the stereoselective preparation of a compound of formula (I), the process consists of process steps (I), (J), (K), (L), and (M) or of process steps (I), (N), (O), (L) and (M), while process steps (I) to (M) in each case take place successively in the order indicated.

Another preferred process for the stereoselective preparation of a compound of formula (II) is characterized in that the process consists of process steps (I), (J), (K) and (L), or of process steps (I), (N), (O) and (L), while process steps (I) to (L) in each case take place successively in the order indicated.

Particularly preferred is process step (G).

Also particularly preferred is process step (I).

The invention further relates to the intermediate of formula (6), optionally in the form of the tautomers, solvates or hydrates thereof.

The invention further relates to the intermediate of formula (7), optionally in the form of the tautomers, solvates or hydrates thereof.

The invention further relates to the intermediate of formula (8), optionally in the form of the tautomers, solvates or hydrates thereof.

The invention further relates to the intermediate of formula (9), optionally in the form of the tautomers, solvates or hydrates thereof.

The invention further relates to the intermediate of formula (11) or (11A), optionally in the form of the tautomers, solvates or hydrates thereof.

The invention further relates to a pharmaceutical composition containing a compound of formula (I). An orally administered pharmaceutical composition containing a compound of formula (I) is preferred.

In another aspect the invention relates to medicament combinations which contain, in addition to a compound of formula (I) according to claim 1, as a further active substance, one or more compounds selected from among the categories of the betamimetics, anticholinergics, corticosteroids, PDE4-inhibitors, LTD4-receptor antagonists, LTB4-receptor antagonists, inhibitors of MAP kinases, bradykinin receptor antagonists, endothelin receptor antagonists, CXCR1 and/or CXCR2 receptor antagonists, and antitussives, or double or triple combinations thereof.

In process steps A, C to L and N alternative reagents may be used, which are selected from among the reagents listed below:

In process step

A: in addition to ethylenediamine and chloroform:
   preferably benzyltriethylammonium chloride/NaOH, tetrabutylammonium chloride/KOH, benzyltriethylammonium chloride/KOH, tetrabutylammonium chloride/NaOH, particularly preferably benzyltriethylammonium chloride/NaOH;

C: preferably alkoxide bases selected from among NaO$^t$Bu, KO$^t$Bu and NaOEt, carbonate bases selected from among Cs$_2$CO$_3$, K$_2$CO$_3$, Li$_2$CO$_3$ and Na$_2$CO$_3$, particularly preferably sodium methoxide;

D: in addition to di-tert-butyldicarbonate and DMAP (4-(dimethylamino)-pyridine):
   preferably K$_2$CO$_3$, Cs$_2$CO$_3$, Li$_2$CO$_3$ and Na$_2$CO$_3$, particularly preferably K$_2$CO$_3$;

E: preferably NaBH$_4$ and LiBH$_4$, particularly preferably NaBH$_4$,

F: in addition to trifluoroacetic anhydride:
   as base preferably triethylamine, Hünig base, N-methylmorpholine and N,N-diethylaniline, particularly preferably triethylamine;

G: in addition to 3-benzyl-6-hydroxy-7-methoxy-3H-quinazolin-4-one:
   preferably triphenylphosphine/diisopropyl azodicarboxylate, triphenylphosphine/diethyl azodicarboxylate, tributylphosphine/1,1'-(azodicarbonyl)dipiperidine, particularly preferably triphenylphosphine/diisopropyl azodicarboxylate;

H: catalysts, preferably selected from among Pd/C and Pd(OH)$_2$, particularly preferably Pd/C;

I: preferably N-chlorosuccinimide/triphenylphosphane (in combination), oxalyl chloride, thionyl chloride, phosphorus oxychloride, phosphorus pentachloride, carbon tetrachloride/triphenylphosphane, dichlorotriphenylphosphorane and P,P-dichlorophenylphosphine oxide, particularly preferably N-chlorosuccinimide/triphenylphosphane (in combination);

J+K: in addition to 3-chloro-2-fluooraniline:
preferably HCl, methanesulphonic acid, ethanesulphonic acid, p-toluenesulphonic acid and HBr, particularly preferably HCl;

L: preferably ethanolamine, ammonia and Ba(OH)$_2$, particularly preferably ethanolamine;

I+N: preferably N-chlorosuccinimide/triphenylphosphane (in combination), HCl, oxalyl chloride, thionyl chloride, phosphorus oxychloride, phosphorus pentachloride, carbon tetrachloride/triphenylphosphane, dichlorotriphenylphosphorane, P,P-dichlorophenylphosphine oxide, methanesulphonic acid, ethanesulphonic acid, p-toluenesulphonic acid and HBr, particularly preferably N-chlorosuccinimide/triphenylphosphane (in combination) and HCl.

The use of the following solvents selected from the group specified in each case is preferred in the process steps described above:

In process step
A: CH$_2$Cl$_2$, CHCl$_3$, THF (tetrahydrofuran) and dioxane;
B: HOAc, dioxane, H$_2$O and aqueous solutions of the following solvents selected from among EtOH, THF, iPrOH, MeOH, NMP(N-methyl-2-pyrrolidone) and DMF (dimethylformamide);
C: ACN(CH$_3$CN), EtOH, MeOH, iPrOH, H$_2$O, THF and NMP;
D: ACN, EtOH and NMP;
E: H$_2$O, MeOH, EtOH, THF and dioxane;
F: Me-THF, THF, toluene, CH$_2$Cl$_2$ and dioxane;
G: THF, NMP, dioxane, DMF and CH$_2$Cl$_2$;
H: iPrOH, dioxane, EtOH, MeOH, THF and NMP;
I: dioxane/ACN and THF/dioxane;
J: ACN, dioxane, THF and EtOH;
K: ACN, dioxane, THF and EtOH;
L: EtOH, MeOH, iPrOH and dioxane;
M: EtOH, MeOH and H$_2$O;
N: dioxane/ACN and THF/dioxane
O: EtOH, n-PrOH, dioxane and NMP The process steps described above are preferably carried out in the following temperature ranges:

In process step:
A: preferably −15 to 40° C., particularly preferably 0 to 20° C.;
B: preferably 0 to 100° C., particularly preferably 75 to 100° C.;
C: preferably 0 to 65° C., particularly preferably 15 to 30° C.;
D: preferably 10 to 80° C., particularly preferably 15 to 35° C.;
E: preferably 0 to 40° C., particularly preferably 0 to 15° C.;
F: preferably −10 to 60° C., particularly preferably 0 to 35° C.;
G: preferably 10 to 65° C., particularly preferably 45 to 60° C.;
H: preferably 20 to 85° C., particularly preferably 70 to 85° C.;
I: preferably 20 to 100° C., particularly preferably 70 to 95° C.;
J: preferably 20 to 100° C., particularly preferably 50 to 85° C.;
K: preferably 20 to 100° C., particularly preferably 50 to 85° C.;
L: preferably 50 to 80° C., particularly preferably 70 to 80° C.;
M: preferably 0 to 75° C., particularly preferably 0 to 70° C.
N: preferably 20 to 100° C., particularly preferably 50 to 85° C.;
O: preferably 50 to 100° C., particularly preferably 70 to 80° C.;

Preferably, protective groups selected from among benzyl, Cbz, trifluoracetyl and Boc, particularly trifluoracetyl and Boc, are used.

The abbreviation Boc used in the above formulae denotes tertiary butyl carbamate and Cbz denotes benzyloxycarbonyl.

Scheme 1 illustrates the synthesis according to the invention. All the compounds are shown in the form of their bases.

Scheme 1 (part 1 of 2) Synthesis of compound (I)

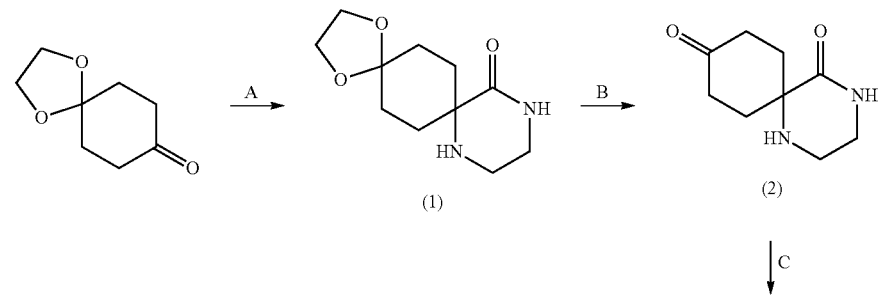

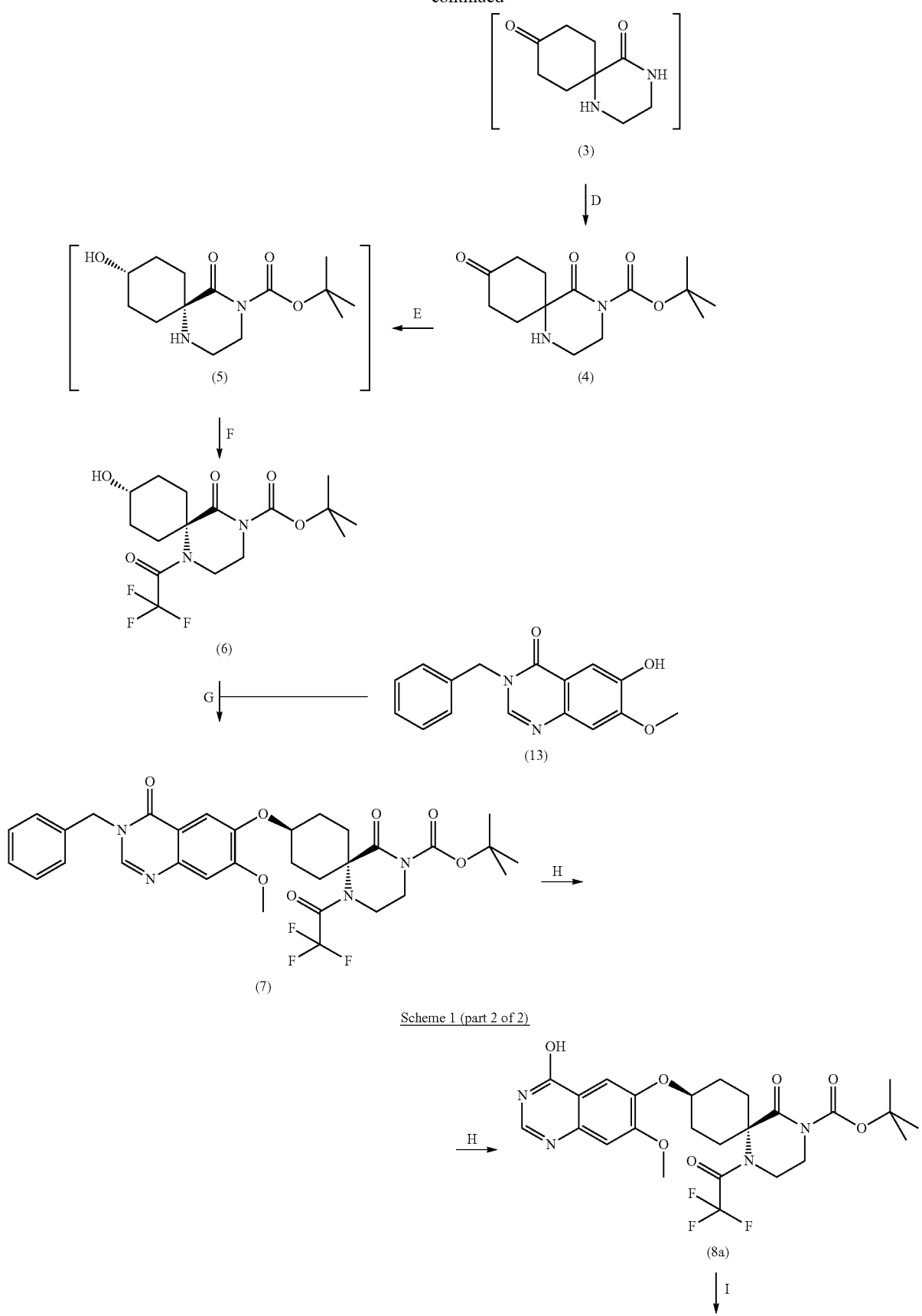

13
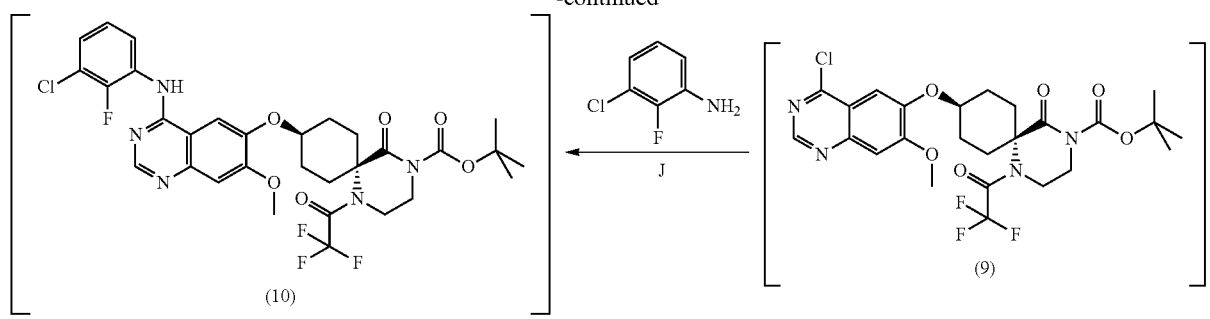
14
-continued
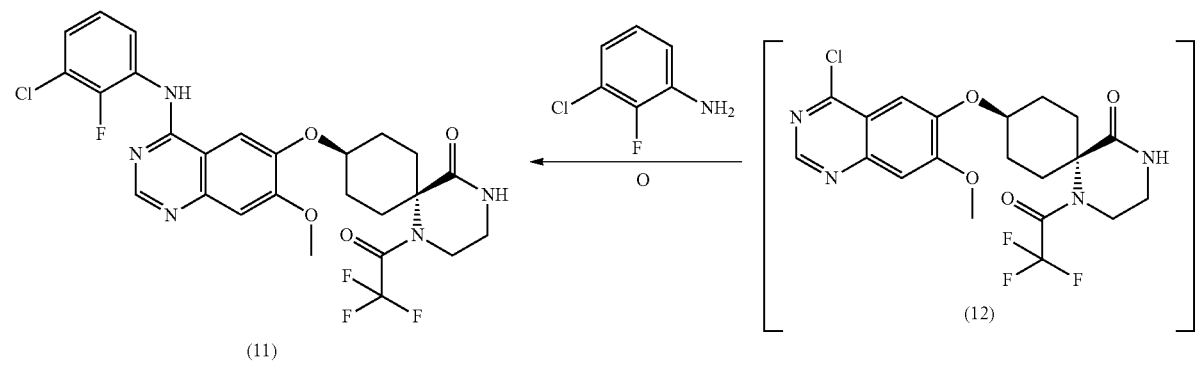
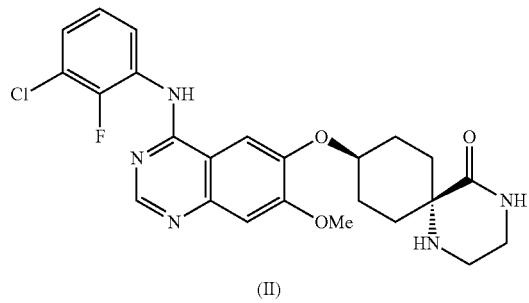
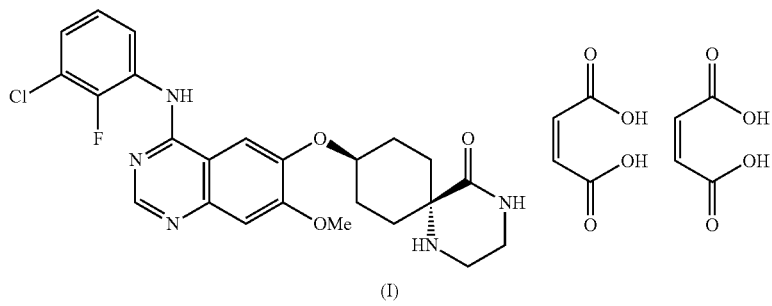

The following Examples serve to illustrate the processes carried out by way of example for preparing the compound of formula (I). These Examples are to be understood as being an illustration of the invention, without limiting it to their subject-matter.

EXAMPLE 1

1,4-dioxa-9,12-diaza-dispiro[4.2.5.2]pentadecan-13-one

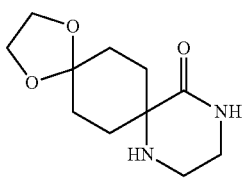

(1)

Process Step A 15.1 kg of 50% sodium hydroxide solution are added dropwise at 5° C. to a mixture of 437 g benzyltriethylammonium chloride and 2700 ml ethylenediamine in 19.2 L dichloromethane. Then a solution of 6000 g of 1,4-cyclohexanedione-mono-ethyleneketal and 6100 g chloroform in 4.8 L dichloromethane within the next 4.5 h is added dropwise at 5-15° C. The dropping funnel is rinsed with 3 L dichloromethane. After 15 h, 18 L water and 39 L dichloromethane are added at 15-25° C. The phases are separated and the aqueous phase is extracted with 20 L dichloromethane. The combined organic phases are concentrated by distillation. After 72 L solvent have been distilled off, 48 L isopropanol are added to the suspension and then a further 30 L solvent are distilled off. After cooling to 3° C. the precipitate is filtered off and washed twice with 7.5 L cold isopropanol. After drying at 50° C. in vacuo, 6144 g of product is obtained.

Mass spectrum (ESI$^+$): m/z=227 [M+H]$^+$

EXAMPLE 2

1,4-diaza-spiro[5.5]undecane-5,9-dione

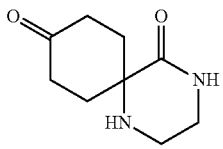

(3)

Process Step B 14.5 kg of 4M HCl in dioxane are added dropwise within 15 min to 6085 g 1,4-dioxa-9,12-diaza-dispiro[4.2.5.2]pentadecan-13-one in 25 kg acetic acid at 80-100° C. The dropping funnel is rinsed with 3 kg acetic acid. After 140 min the suspension is cooled to 20° C. After 2 h the precipitate is filtered off and washed twice with 12 L dioxane. After drying at 60° C. in vacuo, 5333 g of product is obtained as the hydrochloride.

Mass spectrum (ESI$^+$): m/z=183 [M+H]$^+$

Process Step C 5200 g of 1,4-diaza-spiro[5.5]undecane-5,9-dione hydrochloride in 52 L acetonitrile are combined with 4370 ml 30% sodium methoxide solution in methanol at RT within 3 h. The dropping funnel is rinsed with 1 L methanol. 250 g sodium carbonate are added and the mixture is stirred for 16 h. 30 L solvent are distilled off and after the addition of 20 L acetonitrile the suspension is filtered. The filter cake is washed with 10 L acetonitrile. 22 L solvent are distilled off from the filtrate and the residue that contains the product is further reacted directly in the next step.

EXAMPLE 3 tert-butyl 5,9-dioxo-1,4-diaza-spiro[5.5]undecane-4-carboxylate

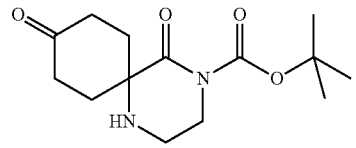

(4)

Process Step D 6573 g potassium carbonate and 145 g 4-(dimethylamino)-pyridine are added to the residue from the previous mixture which contains the 1,4-diaza-spiro[5.5]undecane-5,9-dione. Then within 30 min 6487 g di-tert-butyldicarbonate in 8 L acetonitrile is added dropwise. The dropping funnel is rinsed with 2 L acetonitrile. After 100 min the mixture is added to 20 L water at 10° C. It is rinsed with 2 L water, 5 L acetonitrile and 16 L toluene. After phase separation the organic phase is combined with 10 L toluene. 55 L solvent are distilled off. After the addition of 30 L methylcyclohexane and 10 L toluene the mixture is inoculated with product and the suspension is stirred for 14 h at 20-30° C. 20 L methylcyclohexane are added and the mixture is cooled to −5° C. After 2.5 h the precipitate is filtered off and washed with 10 L methylcyclohexane. After drying at 50° C. in vacuo, 5160 g of product is obtained.

Mass spectrum (ESI$^+$): m/z=283 [M+H]$^+$

EXAMPLE 4 tert-butyl (cis)-9-hydroxy-5-oxo-1,4-diaza-spiro[5.5] undecane-4-carboxylate

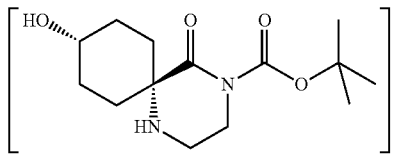

(5)

Process Step E 201 g sodium borohydride in 5 L water are added dropwise at 3° C. within 17 min to a mixture of 5000 g of tert-butyl 5,9-dioxo-1,4-diaza-spiro[5.5]undecane-4-carboxylate in 35 L water. The dropping funnel is rinsed with 1.4 L water. After 15 min, 30 L methyl-tetrahydrofuran are added. After the addition of 10 L of sat. potassium carbonate solution the phases are separated and the aqueous phase is extracted with 20 L methyl-tetrahydrofuran. The combined organic phases are washed with 1 L sat. saline solution. The organic phase is separated off and diluted with 27.5 L methyl-tetrahydrofuran. 55 L solvent are distilled off. Then 15 L methyl-tetrahydrofuran are added and 15 L solvent are distilled off. Then 20 L methyl-tetrahydrofuran are added and 20 L solvent are distilled off. Then 20 L methyl-tetrahydrofuran are added and 20 L solvent are distilled off. The residue which contains the product is further reacted directly in the next step.

Mass spectrum (ESI$^+$): m/z=285 [M+H]$^+$

EXAMPLE 5 tert-butyl(cis)-9-hydroxy-5-oxo-1-(2,2,2-trifluoro-acetyl)-1,4-diaza-spiro[5.5]undecane-4-carboxylate

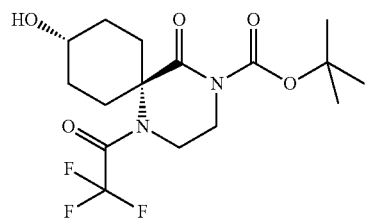

(6)

Process Step F 11.1 L triethylamine are added to the organic phase from the previous mixture. Then 5170 ml trifluoroacetic anhydride are added dropwise within 30 min at 3-25° C. After 15 min 12.4 L methanol are added. After 1 h, 30 L solvent are distilled off in vacuo. Then 15.3 L methanol are added and 8 L of solvent are distilled off in vacuo. 12.4 L methanol are added and 35 L water are added dropwise at 1-10° C. within 50 min. After 1 h at 2° C. the precipitate is centrifuged off and washed with 10 L of a 2:1 mixture of water and methanol and then again washed with 10 L water. After drying at 55° C. in the circulating air dryer 5299 g of product is obtained as a cis/trans mixture.

This crude product is suspended in 70 L toluene. Then 500 ml solvent are distilled off and then 10 L toluene are added. The solution is cooled and at 52° C. it is inoculated with product. After 3 h at 1° C. the precipitate is centrifuged off and washed with 8 L cold toluene. After drying at 55° C. in vacuo 4398 g of product is obtained, which still contains approx. 4% trans product.

Mass spectrum (ESI$^+$): m/z=381 [M+H]$^+$

EXAMPLE 6 tert-butyl(trans)-9-(3-benzyl-7-methoxy-4-oxo-3,4-dihydro-quinazolin-6-yloxy)-5-oxo-1-(2,2,2-trifluoro-acetyl)-1,4-diaza-spiro[5.5]undecane-4-carboxylate

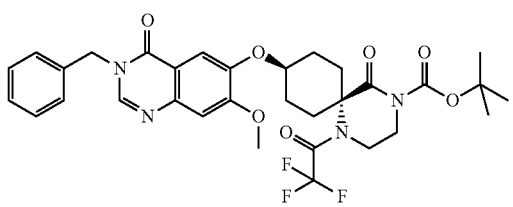

(7)

Process Step G 2471 ml diisopropyl azodicarboxylate is added dropwise, within 100 min, to a mixture of 3500 g tert-butyl (cis)-9-hydroxy-5-oxo-1-(2,2,2-trifluoro-acetyl)-1,4-diaza-spiro [5.5]undecane-4-carboxylate, 2362 g 3-benzyl-6-hydroxy-7-methoxy-3H-quinazolin-4-one and 3292 g triphenylphosphine in 45 L tetrahydrofuran at 50-55° C. The dropping funnel is rinsed with 4 L tetrahydrofuran and 30 L solvent are distilled off in vacuo. Then, during the continuous addition of 60 L ethanol, a further 30 L solvent are distilled off at normal pressure. It is inoculated with product and left to cool slowly to RT. After 19 h, the precipitate is filtered off and washed with 15 L ethanol. After drying at 50° C. in vacuo, 4710 g of product is obtained.

Mass spectrum (ESI$^+$): m/z=645 [M+H]$^+$

EXAMPLE 7 tert-butyl(trans)-9-(4-hydroxy-7-methoxy-quinazolin-6-yloxy)-5-oxo-1-(2,2,2-trifluoro-acetyl)-1,4-diaza-spiro[5.5]undecane-4-carboxylate

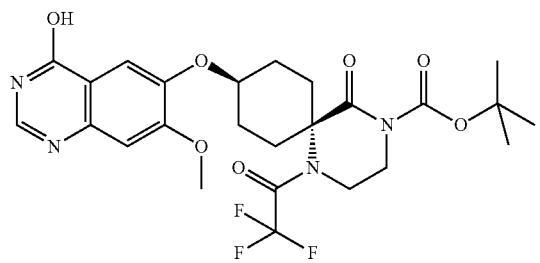

(8a)

-continued (8b)

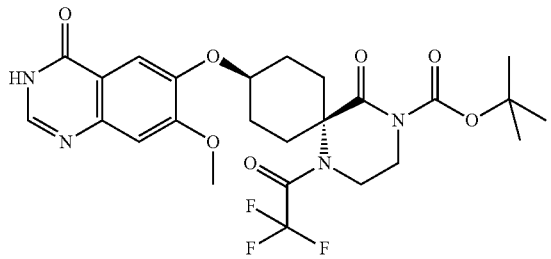

Process Step H 470 g palladium (10%) on charcoal are added to a mixture of 4700 g tert-butyl(trans)-9-(3-benzyl-7-methoxy-4-oxo-3,4-dihydro-quinazolin-6-yloxy)-5-oxo-1-(2,2,2-trifluoro-acetyl)-1,4-diaza-spiro[5.5]undecane-4-carboxylate in 33 L isopropanol and 33 L dioxane. After 4 h hydrogenation at 80° C. the mixture is filtered at 60° C. and washed with a mixture of 10 L isopropanol and 10 L dioxane. 58 L solvent are distilled off from the filtrate in vacuo and 32 L tert-butylmethylether are added. After 2 h at 0-5° C. the precipitate is filtered off and washed with 15 L tert-butylmethylether. After drying at 50° C. in vacuo 4153 g of product is obtained.

Mass spectrum (ESI⁺): m/z=555 [M+H]⁺

EXAMPLE 8 tert-butyl(trans)-9-(4-chloro-7-methoxy-quinazolin-6-yloxy)-5-oxo-1-(2,2,2-trifluoro-acetyl)-1,4-diaza-spiro[5.5]undecane-4-carboxylate (9)

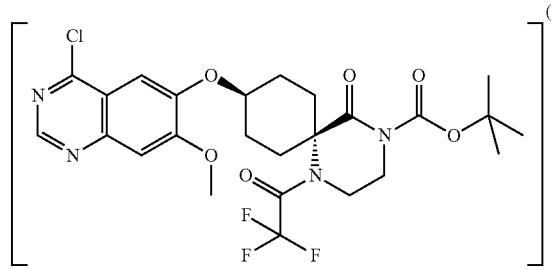

Process Step I 1590 g N-chlorosuccinimide in 20 L acetonitrile are added to a mixture of 5500 g tert-butyl(trans)-9-(4-hydroxy-7-methoxy-quinazolin-6-yloxy)-5-oxo-1-(2,2,2-trifluoro-acetyl)-1,4-diaza-spiro[5.5]undecane-4-carboxylate and 3122 g triphenylphosphine in 24 L dioxane at 60° C. within one minute. The dropping funnel is rinsed with 4 L acetonitrile and the mixture is heated to 80-90° C. for 30 min. The mixture containing the product is used directly in the next step.

EXAMPLE 9 tert-butyl(trans)-9-[4-(3-chloro-2-fluoro-phenylamino)-7-methoxy-quinazolin-6-yloxy]-5-oxo-1-(2,2,2-trifluoro-acetyl)-1,4-diaza-spiro[5.5]undecane-4-carboxylate (10)

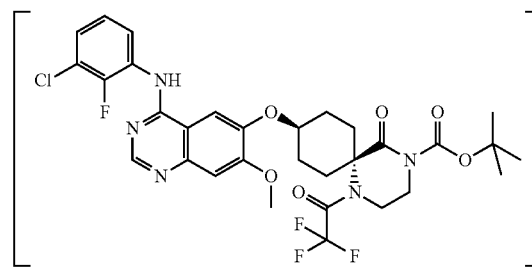

(trans)-9-[4-(3-chloro-2-fluoro-phenylamino)-7-methoxy-quinazolin-6-yloxy]-1-(2,2,2-trifluoro-acetyl)-1,4-diaza-spiro[5.5]undecan-5-one hydrochloride (11A)

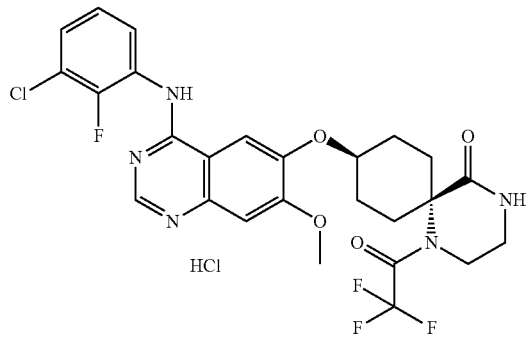

Process Step J+K

After 20 min at 50-60° C. 1733 g 3-chloro-2-fluoraniline are added to the mixture. The dropping funnel is rinsed with 2 L acetonitrile. Then 7.8 kg 4 M hydrochloric acid in dioxane are added and the mixture is stirred for 45 min at 55-80° C. After cooling to 1° C. the precipitate is filtered off and washed with 10 L ethanol. The precipitate is suspended in 40 L ethanol and combined with 290 g 3-chloro-2-fluoroaniline. The suspension is stirred for 45 min at 70-80° C. and then for 13 h at RT. The precipitate is filtered off and washed with 10 L ethanol. After drying at 60° C. in vacuo 4853 g of product is obtained as the hydrochloride.

Mass spectrum (ESI⁺): m/z=582 [M+H]⁺
or:

Process Step O

A mixture of 3.42 g (trans)-9-(4-chloro-7-methoxy-quinazolin-6-yloxy)-1-(2,2,2-trifluoro-acetyl)-1,4-diazaspiro[5.5]undecan-5-one and 1.25 g 3-chloro-2-fluoroaniline in 40 ml of ethanol is heated to 80° C. for 2 h. After the suspension has been cooled to 20° C. and stirred for 16 h the precipitate is filtered off and washed with 10 mL ethanol and 10 mL tert-butylmethylether. After drying at 100° C. in vacuo, 3.28 g of product is obtained.

Mass spectrum (ESI+): m/z=582 [M+H]+

EXAMPLE 10

(trans)-9-[4-(3-chloro-2-fluoro-phenylamino)-7-methoxy-quinazolin-6-yloxy]-1,4-diaza-spiro[5.5] undecan-5-one

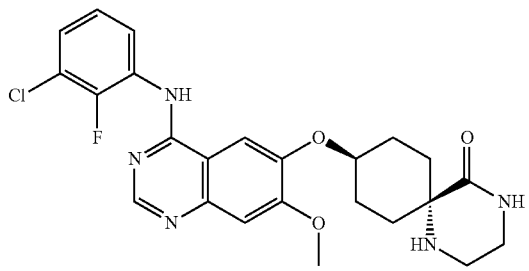

(II)

Process Step L

A mixture of 4700 g (trans)-9-[4-(3-chloro-2-fluoro-phenylamino)-7-methoxy-quinazolin-6-yloxy]-1-(2,2,2-trifluoro-acetyl)-1,4-diaza-spiro[5.5]undecan-5-one and 5150 g ethanolamine in 47 L ethanol is heated to 75-80° C. for 17 h. After the suspension has been cooled to 20° C. the precipitate is filtered off and washed with 15 L ethanol. After drying at 60° C. in vacuo, 3776 g of product is obtained as the mono-ethanol solvate.

Mass spectrum (ESI+): m/z=486 [M+H]+

1H NMR (400 MHz, DMSO): 9.60 (1H, s); 8.37 (1H, s); 7.82 (1H, s); 7.44-7.55 (2H, m), 7.37 (1H, s); 7.28 (1H, t); 7.22 (1H, s); 4.63-4.69 (1H, m); 4.33 (1H, t); 3.96 (3H, s); 3.41-3.49 (2H, m); 3.11-3.16 (2H, m); 2.82-2.87 (2H, m); 2.30 (1H, s); 2.14-2.23 (2H, m); 1.84-1.97 (4H, m); 1.44-1.51 (2H, m); 1.06 (3H, t).

EXAMPLE 11

(trans)-9-[4-(3-chloro-2-fluoro-phenylamino)-7-methoxy-quinazolin-6-yloxy]-1,4-diaza-spiro[5.5] undecan-5-one dimaleic acid compound

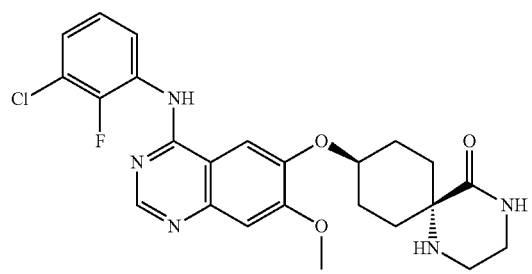 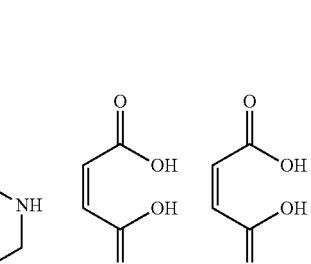

(I)

Process Step M

A solution of 1680 g maleic acid in 7 L ethanol and 7 L water is added at 77° C. to 3500 g (trans)-9-[4-(3-chloro-2-fluoro-phenylamino)-7-methoxy-quinazolin-6-yloxy]-1,4-diaza-spiro[5.5]undecan-5-one mono-ethanol solvate in 18 L of ethanol. The dropping funnel is rinsed with 3 L ethanol. The solution is inoculated with product at 66° C. and after 5 min 35 L ethanol are added dropwise to the suspension. The suspension is cooled to 20° and stirred for 1 h at this temperature. Then it is cooled to 1° C. and stirred for 16 h at this temperature. The precipitate is filtered off and washed twice with 10 L ethanol. After drying at 60° C. in vacuo, 4362 g of product is obtained.

Mass spectrum (ESI+): m/z=486 [M+H]+

1H NMR (400 MHz, DMSO): 8.50 (1H, s); 8.24 (1H, s); 7.93 (1H, s); 7.50-7.57 (2H, m), 7.29-7.35 (1H, m); 7.27 (1H, s); 6.15 (4H, s); 4.65-4.71 (1H, m); 3.98 (3H, s); 3.45-3.51 (2H, m); 3.39-3.44 (2H, m); 2.38-2.48 (2H, m); 2.06-2.15 (2H, m); 1.83-2.02 (4H, m).

EXAMPLE 12

(trans)-9-(4-chloro-7-methoxy-quinazolin-6-yloxy)-1-(2,2,2-trifluoro-acetyl)-1,4-diaza-spiro[5.5]undecan-5-one

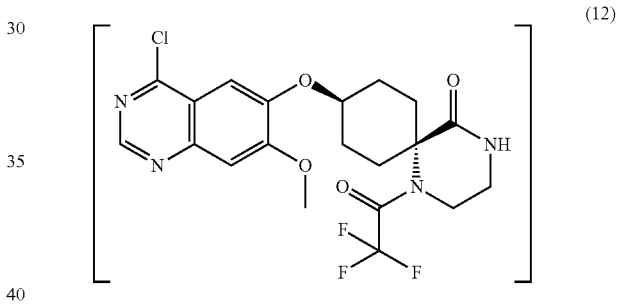

(12)

Process step I+N 19.6 g N-chlorosuccinimide in 240 mL acetonitrile are added at 60° C. within two minutes to a mixture of 60 g tert-butyl(trans)-9-(4-hydroxy-7-methoxy-quinazolin-6-yloxy)-5-oxo-1-(2,2,2-trifluoro-acetyl)-1,4-diaza-spiro[5.5] undecane-4-carboxylate and 37.5 g triphenylphosphine in 300 mL dioxane. The mixture is heated to 80-90° C. for 100 min. After 20 min at 50-60° C., 84 mL of 4 M hydrochloric acid in dioxane are added to the mixture and the mixture is stirred for 3 h at 50-85° C. After stirring for 17 h at ambient temperature the mixture is cooled to 5° C. and the precipitate is filtered off. The filter cake is washed with a 1:1 mixture of dioxane/acetonitrile and with tert-butylmethylether. After drying at 50° C., 40 g of product is obtained.

Mass spectrum (ESI⁺): m/z=473 [M+H]⁺

Collection of Data

The following equipment and test conditions are used to collect the data appended hereto.

X-Ray Powder Diffractometer

STOE Stadi P X-ray powder diffractometer with a location-sensitive detector in transmission mode with a curved germanium (111) primary monochromator; wavelength used: $CuK_{\alpha I}$ with λ=1.540598 Å; operation of the X-ray tube: 40 kV, 40 mA; 2 θ range: 3-40°. The complete X-ray powder diffraction pattern of compound (I) is shown in FIG. 1. The characteristic peak positions for the X-ray powder diffraction pattern of compound (I) is shown in Table 1 below:

TABLE 1

X-ray reflections to 30 °2 Θ inclusive intensities (standardised) of compound (I)

| 2Θ [°] | $d_{hkl}$ [Å] | Intensity $I/I_o$ [%] |
|---|---|---|
| 5.76 | 15.34 | 5 |
| 6.20 | 14.25 | 12 |
| 10.00 | 8.84 | 11 |
| 10.65 | 8.30 | 22 |
| 11.52 | 7.68 | 15 |
| 12.43 | 7.11 | 26 |
| 13.89 | 6.37 | 10 |
| 14.41 | 6.14 | 4 |
| 14.95 | 5.92 | 14 |
| 15.33 | 5.77 | 27 |
| 15.68 | 5.65 | 8 |
| 16.10 | 5.50 | 10 |
| 16.61 | 5.33 | 15 |
| 17.09 | 5.18 | 14 |
| 18.06 | 4.91 | 17 |
| 18.44 | 4.81 | 13 |
| 18.92 | 4.69 | 100 |
| 19.30 | 4.60 | 17 |
| 19.60 | 4.53 | 6 |
| 20.37 | 4.36 | 51 |
| 20.70 | 4.29 | 6 |
| 21.38 | 4.15 | 26 |
| 22.41 | 3.96 | 17 |
| 23.06 | 3.85 | 49 |
| 23.64 | 3.76 | 10 |
| 24.19 | 3.68 | 7 |
| 24.67 | 3.61 | 79 |
| 25.29 | 3.52 | 8 |
| 25.68 | 3.47 | 3 |
| 26.61 | 3.35 | 13 |
| 26.94 | 3.31 | 4 |
| 27.40 | 3.25 | 21 |
| 27.67 | 3.22 | 7 |
| 28.13 | 3.17 | 6 |
| 28.68 | 3.11 | 13 |
| 29.05 | 3.07 | 6 |
| 29.55 | 3.02 | 19 |
| 29.79 | 3.00 | 7 |

Thermoanalysis Equipment

A DSC 822 made by Mettler Toledo is used. The following measuring parameters are used: heating rate: 10 K/min; type of crucible: perforated aluminium crucible; atmosphere: $N_2$, 80 ml/min flux; typical weights: 3-10 mg.

A TGA/SDTA 851 made by Mettler Toledo which is coupled to a Nicolet FT-IR 4700 spectrometer (for analysing the volatile fractions) is used. The following measuring parameters are used: heating rate: 10 K/min; type of crucible: open aluminium oxide crucible; atmosphere: $N_2$, 20 ml/min flux; typical weights: 15-25 mg.

The melting point of compound (I) can be inferred from the DSC/TG schemes in FIG. 2 appended hereto.

Equipment for Water Sorption Tests

A DVS-1 made by Surface Measurement Systems (=SMS) is used to test the hygroscopic characteristics: the following humidity profiles are used: 10-90% r.h. in 10% steps, recording both a sorption and a desorption profile, typical weights: 10-20 mg The corresponding diagrams (kinetic and isothermic plot) of the different forms are shown in FIGS. 3*a*) and *b*).

Biological Test

The biological properties of compound (I) are investigated as follows, for example:

The inhibition of the EGF-R-mediated signal transmission can be demonstrated e.g. with cells which express human EGF-R and whose survival and proliferation depend on stimulation by EGF or TGF-alpha. A murine haematopoietic cell line is genetically modified so as to express functional human EGF-R. The proliferation of this cell line can therefore be stimulated by EGF.

The test is carried out as follows:

The cells are cultivated in RPMI/1640 medium. The proliferation is stimulated with 20 ng/ml of human EGF (Promega). To investigate the inhibitory activity of the compounds according to the invention these compounds are dissolved in 100% dimethylsulfoxide (DMSO) and added to the cultures in various dilutions, the maximum DMSO concentration being 1%. The cultures are incubated for 48 hours at 37° C.

In order to determine the inhibitory activity of compound (I) according to the invention the relative cell number is measured in O.D. units using the Cell Titer 96™ AQueous Non-Radioactive Cell Proliferation Assay (Promega). The relative cell number is calculated as a percentage of the control and the concentration of active substance which inhibits the proliferation of the cells by 50% (IC50) is derived therefrom.

TABLE 2

| Compound | Inhibition of the EGFR-dependent proliferation $IC_{50}$ [nM] |
|---|---|
| (I) | 4 |

Indications

As has been found, the compound of formula (I) is characterized by its versatility in the therapeutic field. Particular mention should be made of the possible applications for which the compound of formula (I) according to the invention is preferably used on the basis of its pharmaceutical efficacy as a tyrosine inhibitor.

The compound of general formula (I) according to the invention thus inhibits signal transduction by tyrosine kinases, as demonstrated by the example of the human EGF receptor, and is therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compound (I) according to the invention is also useful for preventing and treating diseases of the airways and lungs which are accompanied by increased or altered production of mucus caused by stimulation of tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compound (I) is also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome.

In addition, the compound (I) may be used to treat other diseases caused by abnormal function of tyrosine kinases, such as e.g. epidermal hyperproliferation (psoriasis), benign prostatic hyperplasia (BPH), inflammatory processes, diseases of the immune system, hyperproliferation of haematopoietic cells, the treatment of nasal polyps, etc.

Combinations

The compound of formula (I) may be used on its own or in combination with other active substances. These combinations may be administered either simultaneously or sequentially. Optionally the compound of formula (I) may also be used in combination with W, wherein W denotes a pharmacologically active substance and is selected (for example) from among betamimetics, anticholinergics, corticosteroids, PDE4-inhibitors, LTD4-receptor (CysLT1, CysLT2, CysLT3) antagonists, LTB4-receptor (BLT1, BLT2) antagonists, inhibitors of MAP kinases such as for example p38, ERK1, ERK2, JNK1, JNK2, JNK3 or SAP, bradykinin (BK1, BK2) receptor antagonists, endothelin receptor antagonists, CXCR1 and/or CXCR2 receptor antagonists, and anti-tussive substances.

In addition, double or triple combinations of W may be combined with the compounds of formula (I). Examples of combinations of W with the compound of formula (I) might be:

W denotes a betamimetic, combined with an anticholinergic, corticosteroid, PDE4-ihibitor, EGFR-inhibitor or LTD4-receptor antagonist, W denotes an anticholinergic, combined with a betamimetic, corticosteroid, PDE4-inhibitor, EGFR-inhibitor or LTD4-receptor antagonist, W denotes a corticosteroid, combined with a PDE4-inhibitor, EGFR-inhibitor or LTD4-receptor antagonist W denotes a PDE4-inhibitor, combined with an EGFR-inhibitor or LTD4-receptor antagonist W denotes an EGFR-inhibitor, combined with an anticholinergic.

Examples of betamimetics which may be used here preferably include compounds which are selected from among arformoterol, carmoterol, formoterol, indacaterol, salmeterol, albuterol, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramid, tolubuterol, zinterol and 6-hydroxy-8-{1-hydroxy-2-[2-(4-methoxy-phenyl)-1,1-dimethyl-ethylamino]-ethyl}-4H-benzo[1,4]oxazin-3-one, 8-{2-[2-(2,4-difluoro-phenyl)-1,1-dimethyl-ethylamino]-1-hydroxy-ethyl}-6-hydroxy-4H-benzo[1,4]oxazin-3-one, 8-{2-[2-(3,5-difluoro-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 8-{2-[2-(4-fluoro-phenyl)-1,1-dimethyl-ethylamino]-1-hydroxy-ethyl}-6-hydroxy-4H-benzo[1,4]oxazin-3-one, N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide, 8-{2-[1,1-dimethyl-3-(2-oxo-2,3-dihydro-benzimidazol-1-yl)propylamino]-1-hydroxy-ethyl}-6-hydroxy-4H-benzo[1,4]oxazin-3-one, 8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one, 8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one, 8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one, N-[2-hydroxy-5-((1R)-1-hydroxy-2-{2-[4-(2-hydroxy-2-phenyl-ethylamino)-phenyl]-ethylamino}-ethyl)-phenyl]-formamide, 8-hydroxy-5-((1R)-1-hydroxy-2-{2-[4-(6-methoxy-biphenyl-3-ylamino)-phenyl]-ethylamino}-ethyl)-1H-quinolin-2-one, 8-hydroxy-5-[(1R)-1-hydroxy-2-(6-phenethylamino-hexylamino)-ethyl]-1H-quinolin-2-one, 5-[(1R)-2-(2-{4-[4-(2-amino-2-methyl-propoxy)-phenylamino]-phenyl}-ethylamino)-1-hydroxy-ethyl]-8-hydroxy-1H-quinolin-2-one, [3-(4-{6-[(2R)-2-hydroxy-2-(4-hydroxy-3-hydroxymethyl-phenyl)-ethylamino]hexyloxy}-butyl)-5-methyl-phenyl]-urea, 4-((1R)-2-{6-[2-(2,6-dichloro-benzyloxy)-ethoxy]-hexylamino}-1-hydroxy-ethyl)-2-hydroxymethyl-phenol, 3-(4-{6-[(2R)-2-hydroxy-2-(4-hydroxy-3-hydroxymethyl-phenyl)-ethylamino]-hexyloxy}-butyl)-benzenesulphonamide, 3-(3-{7-[(2R)-2-hydroxy-2-(4-hydroxy-3-hydroxymethyl-phenyl)-ethylamino]heptyloxy}-propyl)-benzenesulphonamide, 4-((1R)-2-{6-[4-(3-cyclopentanesulphonyl-phenyl)-butoxy]-hexylamino}-1-hydroxy-ethyl)-2-hydroxymethyl-phenol, N-1-adamantanyl-2-{3-[(2R)-2-({(2R)-2-hydroxy-2-[4-hydroxy-3-(hydroxymethyl)phenyl]ethyl}amino) propyl]phenyl}acetamide, (1R)-5-{2-[6-(2,2-difluoro-2-phenyl-ethoxy)-hexylamino]-1-hydroxy-ethyl}-8-hydroxy-1H-quinolin-2-one, (R,S)-4-(2-{[6-(2,2-difluoro-4-phenylbutoxy)hexyl]amino}-1-hydroxy-ethyl)-2-(hydroxymethyl)phenol, (R,S)-4-(2-{[6-(2,2-difluoro-2-phenylethoxy)hexyl]amino}-1-hydroxy-ethyl)-2-(hydroxymethyl)phenol, (R,S)-4-(2-{[4,4-difluoro-6-(4-phenylbutoxy)hexyl]amino}-1-hydroxy-ethyl)-2-(hydroxymethyl)phenol, (R,S)-4-(2-{[6-(4,4-difluoro-4-phenylbutoxy)hexyl]amino}-1-hydroxy-ethyl)-2-(hydroxymethyl)phenol, (R,S)-5-(2-{[6-(2,2-difluoro-2-phenylethoxy)hexyl]amino}-1-hydroxy-ethyl)-8-hydroxyquinolin-2(1H)-one, (R,S)-[2-({6-[2,2-difluoro-2-(3-methylphenyl)ethoxy]hexyl}amino)-1-hydroxyethyl]-2-(hydroxymethyl)phenol, 4-(1R)-2-{[6-(2,2-difluoro-2-phenylethoxy)hexyl]amino}-1-hydroxyethyl)-2-(hydroxymethyl)phenol, (R,S)-2-(hydroxymethyl)-4-(1-hydroxy-2-{[4,4,515-tetrafluoro-6-(3-phenylpropoxy) hexyl]amino}ethyl)phenol, (R,S)-5-(2-{[6-(2,2-difluoro-2-phenylethoxy)hexyl]amino}-1-hydroxy-ethyl)-2-hydroxyphenyl]formamide, (R,S)-4-[2-({6-[2-(3-bromophenyl)-2,2-difluoroethoxy]hexyl}amino)-1-hydroxyethyl]-2-(hydroxymethyl)phenol, (R,S)—N-[3-(1,1- difluoro-2-{[6-({2-hydroxy-2-[4-hydroxy-3-(hydroxymethyl)phenyl]ethyl}amino)hexyl]oxy}ethyl)phenyl]-urea, 3-[3-(1,1-difluoro-2-{[6-({2-hydroxy-2-[4-hydroxy-3-(hydroxymethyl)phenyl]ethyl}-amino)hexyl]oxy}phenyl]imidazolidin-2,4-dione, (R,S)-4-[2-({6-[2,2-difluoro-2-(3-methoxyphenyl)ethoxy]hexyl}amino)-1-hydroxyethyl]-2-(hydroxymethyl)phenol, 5-((1R)-2-{[6-(2,2-difluoro-2-phenylethoxy)hexyl]amino}-1-hydroxyethyl)-8-hydroxyquinolin-2(1H)-one, 4-((1R)-2-{[4,4-difluoro-6-(4-phenylbutoxy)hexyl]amino}-1-hydroxy-ethyl)-2-(hydroxymethyl)phenol, (R,S)-4-(2-{[6-(3,3-difluoro-3-phenylpropoxy)hexyl]amino}-1-hydroxy-ethyl)-2-(hydroxymethyl)phenol, (R,S)-(2-{[6-(2,2-difluoro-2-phenylethoxy)-4,4-difluorohexyl]amino}-1-hydroxyethyl)-2-(hydroxymethyl)phenol, (R,S)-4-(2-{[6-(2,2-difluoro-3-phenylpropoxy)hexyl]amino}-1-hydroxy ethyl)-2-(hydroxymethyl)phenol, 3-[2-(3-chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide, N-(2-diethylamino-ethyl)-N-{2-[2-(4-hydroxy-2-oxo-2,3-dihydro-benzothiazol-7-yl)-ethylamino]-ethyl}-3-(2-naphthalen-1-ylethoxy)-propionamide 7-[2-(2-{3-[2-(2-chloro-phenyl)-ethylamino]-propylsulphanyl}-ethylamino)-1-hydroxy-ethyl]-4-hydroxy-3H-benzothiazole-2-one,
optionally in the form of the racemates, enantiomers, diastereomers and optionally in the form of the pharmacologically acceptable acid addition salts, solvates or hydrates thereof. Preferably, according to the invention, the acid addition salts of the betamimetics are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of anticholinergics which may be used here preferably include compounds which are selected from among: tiotropium salts, preferably the bromide salt, oxitropium salts, preferably the bromide salt, flutropium salts, preferably the bromide salt, ipratropium salts, preferably the bromide salt, aclidinium salts, preferably the bromide salt, glycopyrronium salts, preferably the bromide salt, trospium salts, preferably the chloride salt, tolterodine, (3R)-1-phenethyl-3-(9H-xanthen-9-carbonyloxy)-1-azoniabicyclo[2,2,2]octanesalts. In the above-mentioned salts the cations are the pharmacologically active constituents. As X⁻ anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other specified compounds are: tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide; tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide; tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate-methobromide, scopine 9-methyl-xanthene-9-carboxylate-methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide. The above-mentioned compounds may also be used as salts within the scope of the present invention, while instead of the methobromide, the metho-X salts may be used wherein X may have the meanings given hereinbefore for X⁻.

Compounds which may be used as corticosteroids are preferably those selected from among: beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, tipredane and pregna-1,4-diene-3.20-dione, 6-fluoro-11-hydroxy-16,17-[(1-methylethylidene)bis(oxy)]-21-[[4-[(nitrooxy)methyl]benzoyl]oxy]-, (6-alpha, 11-beta,16-alpha)-(9Cl) (NCX-1024), 16,17-butyldenedioxy-6,9-difluoro-11-hydroxy-17-(methylthio)androst-4-en-3-one (RPR-106541), (S)-fluoromethyl 6,9-difluoro-17-[(2-furanylcarbonyl)oxy]-11-hydroxy-16-methyl-3-oxo-androsta-1,4-diene-17-carbothionate, (S)-(2-oxo-tetrahydro-furan-3S-yl) 6,9-difluoro-11-hydroxy-16-methyl-3-oxo-17-propionyloxy-androsta-1,4-dien-17-carbothionate, cyanomethyl 6-alpha,9-alpha-difluoro-11-beta-hydroxy-16alpha-methyl-3-oxo-17alpha(2,2,3,3-tetramethylcyclopropylcarbonyl)oxy-androsta-1,4-diene-17beta-carboxylate, optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, apremilast, arofyllin, atizoram, oglemilast, tetomilast, and 5-[(N-(2,5-dichloro-3-pyridinyl)-carboxamide]-8-methoxy-quinoline (D-4418), N-(3,5-dichloro-1-oxido-4-pyridinyl)-carboxamide]-8-methoxy-2-(trifluoromethyl)-quinoline (D4396 (Sch-351591)), N-(3,5-dichloropyrid-4-yl)-[1-(4-fluorobenzyl)-5-hydroxy-indol-3-yl]glyoxylic acid amide (AWD-12-281 (GW-842470)), 9-[(2-fluorophenyl)methyl]-N-methyl-2-(trifluoromethyl)-9H-purin-6-amine (NCS-613), 4-[(2R)-2-[3-(cyclopentyloxy)-4-methoxyphenyl]-2-phenylethyl]-pyridine (CDP-840), N-[(3R)-3,4,6,7-tetrahydro-9-methyl-4-oxo-1-phenylpyrrolo[3,2,1-jk][1,4]benzodiazepin-3-yl]-4-pyridinecarboxamide (PD-168787), 4-[6,7-diethoxy-2,3-bis(hydroxymethyl)-1-naphthalenyl]-1-(2-methoxyethyl)2(1H)-pyridinone (T-440), 2-[4-[6,7-diethoxy-2,3-bis(hydroxymethyl)-1-naphthalenyl]-2-pyridinyl]-4-(3-pyridinyl)-1(2H)-phthalazinone (T-2585), (3-(3-cyclopenyloxy-4-methoxybenzyl)-6-ethylamino-8-isopropyl-3H-purine (V-11294A), beta-[3-(cyclopentyloxy) 4-methoxyphenyl]-1,3-dihydro-1,3-dioxo-2H-isoindole-2-propanamide (CDC-801), imidazo[1,5-a]pyrido[3,2-e] pyrazin-6(5H)-one, 9-ethyl-2-methoxy-7-methyl-5-propyl- (D-22888), 5-[3-(cyclopentyloxy)-4-methoxyphenyl]-3-[(3-methylphenyl)methyl], (3S,5S)-2-piperidinone (HT-0712), 4-[1-[3,4-bis(difluoromethoxy)phenyl]-2-(3-methyl-1-oxido-4-pyridinyl)ethyl]-alpha,alpha-bis(trifluoromethyl)-benzenemethanol (L-826141), N-(3,5-dichloro-1-oxo-pyridin-4-yl)-4-difluoromethoxy-3-cyclopropylmethoxybenzamide, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], (R)(+)-ethyl[4-(3-cyclopentyloxy-4-methoxyphenyl)pyrrolidin-2-ylidene] acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine, 9-cyclopentyl-5,6-dihydro-7-ethyl-3-(tert-butyl)-9H-pyrazolo[3,4-c]-1,2,4-triazolo[4,3-a]pyridine,
optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTB4-receptor antagonists used here are preferably compounds selected from among for example amebulant (=ethyl [[4-[[3-[[4-[1-(4-hydroxyphenyl)-1-methylethyl]phenoxy] methyl]phenyl]methoxy]phenyl]iminomethyl]-carbamate), optionally in the form of the racemates, enantiomers, diastereomers thereof and optionally in the form of the pharmacologically acceptable acid addition salts, solvates, prodrugs or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTD4-receptor antagonists used here are preferably compounds selected from among montelukast, pranlukast, zafirlukast, and (E)-8-[2-[4-[4-(4-fluorophenyl)butoxy]phenyl]ethenyl]-2-(1H-tetrazol-5-yl)-4H-1-benzopyran-4-one (MEN-91507), 4-[6-acetyl-3-[3-(4-acetyl-3-hydroxy-2-propylphenylthio)propoxy]-2-propylphenoxy]butyric acid (MN-001), 1-(((R)-(3-(2-(6,7-difluoro-2-quinolinyl)ethenyl) phenyl)-3-(2-(2-hydroxy-2-propyl)phenyl)thio)methylcyclopropaneacetic acid, 1-(((1R)-3(3-(2-(2,3-dichlorothieno [3,2-b]pyridin-5-yl)-(E)-ethenyl)phenyl)-3-(2-(1-hydroxy-1-methylethyl)phenyl)propyl)thio)methyl) cyclopropaneacetic acid, [2-[[2-(4-tert-butyl-2-thiazolyl)-5-benzofuranyl]oxymethyl]phenyl]acetic acid optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

By salts or derivatives which the LTD4-receptor antagonists are optionally capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

MAP Kinase inhibitors used are preferably compounds selected from among:
bentamapimod (AS-602801), doramapimod (BIRB-796), 5-carbamoylindole (SD-169), 6-[(aminocarbonyl)(2,6-difluorophenyl)amino]-2-(2,4-difluorophenyl)-3-pyridinecarboxamide (VX-702), alpha-[2-[[2-(3-pyridinyl)ethyl] amino]-4-pyrimidinyl]-2-benzothiazoleacetonitrile (AS-601245), 9,12-epoxy-1H-diindolo[1,2,3-fg:3',2',1'-kl] pyrrolo[3,4-i][1.6]benzodiazocine10-carboxylic acid (CEP-1347), 4-[3-(4-chlorophenyl)-5-(1-methyl-4-piperidinyl)-1H-pyrazole4-yl]-pyrimidine (SC-409),
optionally in the form of the racemates, enantiomers, diastereomers thereof and optionally in the form of the pharmacologically acceptable acid addition salts, prodrugs, solvates or hydrates thereof.

Bradykinin receptor antagonists that may be used are preferably compounds selected from among icatibant and 1-piperazinepentanaminium, delta-amino-4-[[4-[[[2,4-dichloro-3-[[(2,4-dimethyl-8-quinolinyl)oxy]methyl]phenyl] sulphonyl]amino]tetrahydro-2H-pyran-4-yl]carbonyl]-N,N, N-trimethyl-ε-oxo, chloride, hydrochloride (1:1:1), (deltaS)- (MEN-16132), optionally in the form of the racemates, enantiomers and diastereomers thereof and optionally in the form of the pharmacologically acceptable acid addition salts, prodrugs, solvates or hydrates thereof.

Endothelin antagonists that may be used are preferably compounds selected from among actelion-1, ambrisentan, sitaxsentan, N-(2-acetyl-4,6-dimethylphenyl)-3-[[(4-chloro-3-methyl-5-isoxazolyl)amino]sulphonyl]-2-thiophenecarboxamide (TBC-3214) and bosentan, optionally in the form of the racemates, enantiomers and diastereomers thereof and optionally in the form of the pharmacologically acceptable acid addition salts, prodrugs, solvates or hydrates thereof.

Antitussive substances that may be used are preferably compounds selected from among hydrocodone, caramiphen, carbetapentane and dextramethorphan, optionally in the form of the racemates, enantiomers and diastereomers thereof and optionally in the form of the pharmacologically acceptable acid addition salts, prodrugs, solvates or hydrates thereof.

Substances of preferred CXCR1 and/or CXCR2 receptor antagonists that may be used are preferably compounds such as e.g. 3-[[3-[(dimethylamino)carbonyl]-2-hydroxyphenyl] amino]-4-[[(R)-1-(5-methylfuran-2-yl)propyl]amino]cyclobut-3-ene-1,2-dione (SCH-527123),
optionally in the form of the racemates, enantiomers and diastereomers thereof and optionally in the form of the pharmacologically acceptable acid addition salts, prodrugs, solvates or hydrates thereof.

It is preferable, according to the invention, to use the acid addition salts of the above-mentioned betamimetics, anticholinergics, corticosteroids, PDE4 inhibitors, LTB4 (BLT1, BLT2) receptor antagonists, LTD4 (CysLT1, CysLT2, CysLT3) receptor antagonists, inhibitors of MAP kinases such as for example p38, ERK1, ERK2, JNK1, JNK2, JNK3 or SAP, bradykinin receptor antagonists, endothelin receptor antagonists, antitussive substances, CXCR1 and/or CXCR2 receptor antagonists also selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Pharmaceutical Compositions

The compound according to the invention may be administered by oral, transdermal, inhalative, parenteral or sublingual route. The compound according to the invention is present as an active ingredient in conventional preparations, for example in compositions consisting essentially of an inert pharmaceutical carrier and an effective dose of the active substance, such as for example tablets, coated tablets, capsules, wafers, powders, solutions, suspensions, emulsions, syrups, suppositories, transdermal systems etc. An effective dose of the compound according to the invention for oral administration is between 0.1 and 5000, preferably between 1 and 500, particularly preferably between 5-300 mg/dose, when administered by intravenous, subcutaneous or intramuscular route between 0.001 and 50, preferably between 0.1 and 10 mg/dose. For Inhalation, according to the invention suitable solutions are those that contain 0.01 to 1.0, preferably 0.1 to 0.5% of active substance. For inhalative administration the use of powders, ethanolic or aqueous solutions is preferred. It is also possible to use the compound according to the invention as an infusion solution, preferably in a physiological saline solution or nutrient solution.

The compound according to the invention may be used on its own or in conjunction with other active substances according to the invention, optionally also in conjunction with other pharmacologically active substances. Suitable formulations include, for example, tablets, capsules, suppositories, solutions, syrups, emulsions or dispersible powders. Corresponding tablets may be obtained for example by mixing the active substance(s) with known excipients, for example inert diluents, such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

For pharmaceutical use the compound according to the invention is generally used for warm-blooded vertebrates, particularly humans, in doses of 0.01-100 mg/kg of body weight, preferably 0.1-15 mg/kg. For administration it may be formulated for example with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof to produce conventional galenic preparations such as plain or coated tablets, capsules, powders, suspensions, solutions, sprays or suppositories.

The Examples which follow illustrate the present invention without restricting its scope:

Examples of Pharmaceutical Formulations

A) Coated Tablets Containing 75 mg of Active Substance
Composition:

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl-pyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

B) Tablets Containing 100 mg of Active Substance
Composition:

| 1 tablet contains: | |
|---|---|
| active substance | 100.0 mg |
| lactose | 80.0 mg |

-continued

| 1 tablet contains: | |
|---|---|
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

C) Tablets Containing 150 mg of Active Substance

Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

D) Hard Gelatine Capsules Containing 150 mg of Active Substance

Composition:

| 1 capsule contains: | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

E) Suppositories Containing 150 mg of Active Substance

Composition:

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

F) Suspension Containing 50 mg of Active Substance

Composition:

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

G) Ampoules Containing 10 mg Active Substance

Composition:

| active substance | 10.0 mg |
|---|---|
| 0.01N hydrochloric acid | q.s. |
| double-distilled water | ad 2.0 ml |

Preparation:

The active substance is dissolved in the necessary amount of 0.01N HCl, made isotonic with common salt, filtered sterile and transferred into 2 ml ampoules.

H) Ampoules Containing 50 mg of Active Substance

Composition:

| active substance | 50.0 mg |
|---|---|
| 0.01N hydrochloric acid | q.s. |
| double-distilled water | ad 10.0 ml |

Preparation:

The active substance is dissolved in the necessary amount of 0.01N HCl, made isotonic with common salt, filtered sterile and transferred into 10 ml ampoules.

The invention claimed is:
1. A crystalline compound of formula (I)

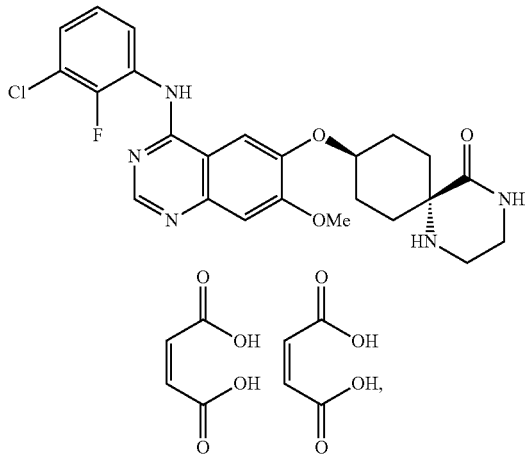

characterized in that reflections in the X-ray powder diagram occur at $d_{hkl}$ values of 7.11, 5.77, 4.69, 4.36, 4.15, 3.85 and 3.61 Å, optionally in the form of the tautomers thereof.

2. The crystalline compound of formula (I) according to claim 1, further characterized in that its X-ray powder diffraction pattern comprises peaks at 12.43, 15.33, 18.92, 20.37, 21.38 and 24.67 degrees 2θ when measured using CuKα radiation.

3. A pharmaceutical composition containing the compound of formula (I) according to claim 1.

4. A pharmaceutical composition which contains the compound of formula (1) according to claim 1 and one or more compounds selected from among the categories of the betamimetics, anticholinergics, corticosteroids, PDE4-inhibitors, LTD4-receptor antagonists, LTB4-receptor antagonists, inhibitors of MAP kinases, bradykinin receptor antagonists, endothelin receptor antagonists, CXCR1 and/or CXCR2 receptor antagonists and antitussives, or double or triple combinations thereof.

* * * * *